(12) United States Patent
Lee et al.

(10) Patent No.: US 10,203,270 B2
(45) Date of Patent: Feb. 12, 2019

(54) MICRO-FLUID MEASURING APPARATUS WITH AN ACTUATOR AND A TUNING FORK

(71) Applicant: SOGANG UNIVERSITY RESEARCH FOUNDATION, Seoul (KR)

(72) Inventors: Jungchul Lee, Seoul (KR); Donghyuk Lee, Uiwang-si (KR); Sangken Kauh, Seoul (KR); Joonhui Kim, Seoul (KR); Nam-Joon Cho, Singapore (SG)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 116 days.

(21) Appl. No.: 15/433,476

(22) Filed: Feb. 15, 2017

(65) Prior Publication Data

US 2018/0003605 A1 Jan. 4, 2018

(30) Foreign Application Priority Data

Jun. 30, 2016 (KR) .................. 10-2016-0082751

(51) Int. Cl.
*G01N 9/00* (2006.01)
*B01L 3/00* (2006.01)
*G01N 15/10* (2006.01)

(52) U.S. Cl.
CPC ............ *G01N 9/002* (2013.01); *B01L 3/5027* (2013.01); *G01N 15/1056* (2013.01);
(Continued)

(58) Field of Classification Search
CPC .............. G01N 29/022; G01N 29/222; G01N 2291/0427; G01N 2009/006; G01N 2015/1087
See application file for complete search history.

(56) References Cited

U.S. PATENT DOCUMENTS 3,903,731 A * 9/1975 Sieben ................... G01N 11/16
73/32 A
3,921,622 A * 11/1975 Cole .................... A61M 1/3626
600/437

(Continued)

FOREIGN PATENT DOCUMENTS

CN 104880411 A * 9/2015 ............. G01N 21/17
KR 10-2016-0070474 A 6/2016
WO WO-0049386 A3 * 12/2000 ......... G01N 15/1227

OTHER PUBLICATIONS

Donghyuk Lee et al., "Nanoliter level liquid density measurements using microtube resonance detection via quartz tuning fork", 2016 KMEMS, Apr. 7, 2016.
(Continued)

*Primary Examiner* — David A Rogers
(74) *Attorney, Agent, or Firm* — Rabin & Berdo, P.C.

(57) ABSTRACT

It is an object of the present invention to provide a measuring apparatus having a reduced size by a substitution of an optical measuring device. A measuring apparatus for measuring micro-fluid or floating particles therein according to an embodiment of the present invention includes: a microtube containing the micro-fluid; an actuator vibrating the micro-tube; and a tuning fork converting vibration of the micro-tube into an electrical signal.

8 Claims, 2 Drawing Sheets

(52) U.S. Cl.
CPC . *B01L 3/502707* (2013.01); *B01L 2200/0647* (2013.01); *B01L 2300/0838* (2013.01); *B01L 2400/0421* (2013.01); *B01L 2400/0439* (2013.01); *G01N 2009/006* (2013.01)

(56) References Cited

U.S. PATENT DOCUMENTS

| | | | | |
|---|---|---|---|---|
| 4,068,521 | A * | 1/1978 | Cosentino | A61B 8/481 600/437 |
| 4,526,480 | A * | 7/1985 | Ward | G01N 9/002 374/117 |
| 6,935,010 | B2 * | 8/2005 | Tadigadapa | G01F 1/8404 29/592.1 |
| 7,047,809 | B2 * | 5/2006 | Cobb | G01N 29/032 73/599 |
| 7,661,293 | B2 * | 2/2010 | Dam | G01N 29/032 73/19.03 |
| 2002/0047697 | A1 * | 4/2002 | Husher | G01N 15/1227 324/71.1 |
| 2004/0074302 | A1 * | 4/2004 | Matsiev | G01H 13/00 73/579 |
| 2007/0217973 | A1 * | 9/2007 | Tao | G01N 29/036 422/243 |
| 2010/0329932 | A1 * | 12/2010 | Yorita | G01N 29/022 422/82.01 |
| 2013/0192349 | A1 * | 8/2013 | Ramkumar | G01N 29/022 73/54.41 |
| 2016/0209367 | A1 * | 7/2016 | Yazdanpanah | G01N 29/022 |

OTHER PUBLICATIONS

Dongeun Huh et al., "Microfluidics for flow cytometric analysis of cells and particles", Physiological Measurement, vol. 26, No. 3, R73-R98, Feb. 1, 2005.

Riushop, "Device and method for measuring microparticles and manufacturing method thereof", Feb. 29, 2016, (with partial translation); http://www.iuchem.co.kr/bbs/board.php?bo_table=patent&wr_id=99.

* cited by examiner

MICRO-FLUID MEASURING APPARATUS WITH AN ACTUATOR AND A TUNING FORK

CROSS-REFERENCE TO RELATED APPLICATION

This application claims priority to and the benefit of Korean Patent Application No. 10-2016-0082751 filed in the Korean Intellectual Property Office on Jun. 30, 2016, the entire contents of which are incorporated herein by reference.

STATEMENT REGARDING PRIOR DISCLOSURES BY THE INVENTOR OR A JOINT INVENTOR

Applicant hereby states under 37 CFR 1.77(b)(6) that Donghyuk Lee, Joonhui Kim, Nam-Joon Cho, Sangken Kauh, Jungchul Lee, *Nanoliter level liquid density measurements using microtube resonance detection via quartz tuning fork*, 2016 KMEMS, published on Apr. 7, 2016, is designated as a grace period inventor disclosure. The disclosure: (1) was made one year or less before the effective filing date of the claimed invention; (2) names the inventor or a joint inventor as an author; and (3) does not name additional persons as authors on a printed publication.

TECHNICAL FIELD

The present invention relates to a measuring apparatus for measuring micro-fluid or floating particles thereof.

BACKGROUND ART

A flow cytometry technology is generally known as a technology for measuring number and physical, chemical, biological characteristics of cells, entities and various biological particles suspended in liquid, and has been used as an important technology for a long time for analyzing characteristics of a great number of cells or micro-particles passing through a narrow area within a micro tube. A method for recognizing phenomenon that cells or micro-particles pass through a micro-tube may be divided into an optical method and an electrical method. The optical method was disclosed in Physiol. Meas. 26, R73-R98 by D. Huh et al.

The optical method measures micro-fluid such as cells or micro-particles passing through a micro-tube using an optical measuring device in a type of laser reflection or transmission.

However, the optical measuring device is difficult to be packed in vacuum due to its big size and is also difficult to be transplanted to other measuring system. Also, the micro-tube is generally formed via a MEMS (Micro Electro Mechanical Systems) process which is a technology for manufacturing a subminiature precision instrument, and this process is very complicated so that a manufacturing cost thereof is high and a yielding rate is poor.

DETAILED DESCRIPTION OF THE INVENTION

Technical Problem

It is an object of the present invention to provide a measuring apparatus having a reduced size by a substitution of an optical measuring device.

It is another object of the present invention to provide a measuring apparatus which can make a micro-tube via simple processes.

Technical Solution

A measuring apparatus for measuring micro-fluid or floating particles therein according to an embodiment of the present invention includes: a micro-tube containing the micro-fluid; an actuator vibrating the micro-tube; and a tuning fork converting vibration of the micro-tube into an electrical signal.

The measuring apparatus may further include: a first injection capillary tube and a second injection capillary tube respectively communicating with both ends of the micro-tube so as to inject the micro-fluid into the micro-tube; and fixing portions fixing the first and the second injection capillary tubes.

The actuator may be a piezo-injector which contacts a surface of the micro-tube and applies pressure in a specific direction.

The tuning fork may be a quartz tuning fork which contacts a surface of the micro-tube and is made of quartz to have a piezoelectric effect.

The quartz tuning fork may receive Fy component among reactive forces generated by a longitudinal axis extension Ft (Fx, Fy) which is applied to the micro-tube by the piezo-actuator and may convert the same into an electrical signal.

The micro-tube may be formed by a plastic working in which a glass capillary tube is melted by a laser heating and is then pulled.

The micro-tube and the first and the second injection capillary tube may be integrally formed.

The micro-tube may be an elongated portion in case that the micro-tube is formed by melting a glass capillary tube by a laser heating and then pulling the same to be elongated, and the first and the second injection capillary tubes may be both end portions of the glass micro-tube which are not elongated by being pulled.

Advantageous Effects

According to an embodiment of the present invention, the conventional optical measurement device can be replaced with the tuning fork, so the volume can be reduced compared to that of the optical measuring device, and thus it can be easily implanted to other measuring system and can be easily packed in vacuum.

Also, according to an embodiment of the present invention, since the micro-tube is made by a plastic working in which the glass capillary tube is melted by laser hearing and then is pulled, the manufacturing process is simple compared to the MEMS process of the conventional art so that the manufacturing cost can be reduced ant the yielding rate can be enhanced.

DETAILED DESCRIPTION OF THE EMBODIMENTS

An embodiment of the present invention will be described with reference to the accompanying drawings hereinafter.

Figure 1:
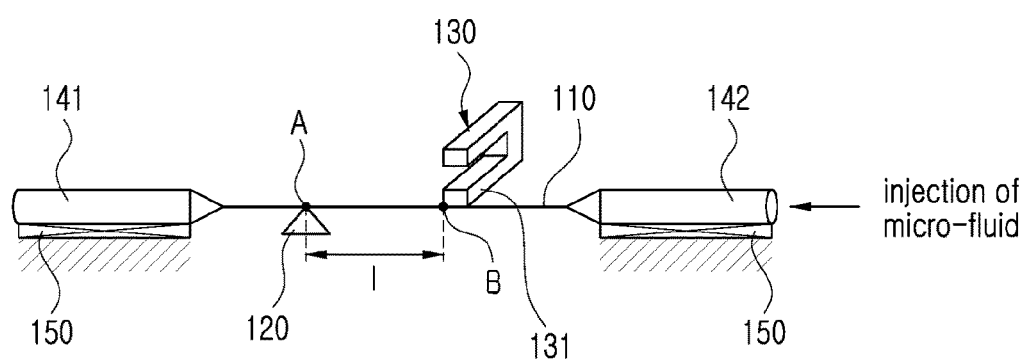
FIG. 1 schematically shows a measuring device according to an embodiment of the present invention.
Figure 2:
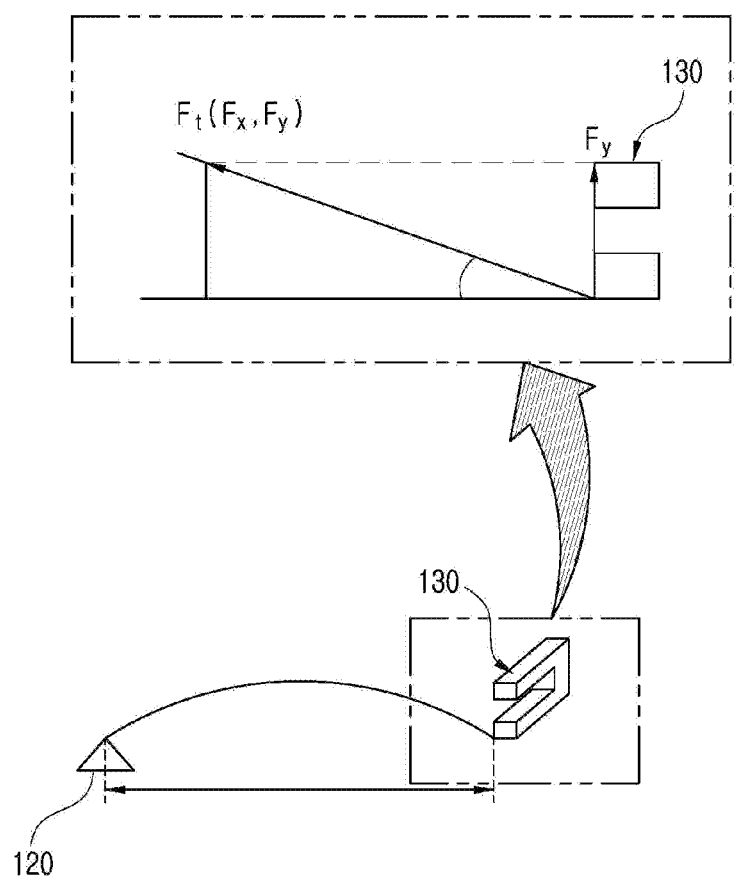
FIG. 2 is a drawing for explaining a measuring principle of a measuring apparatus of FIG. 1.

FIG. 1 schematically shows a measuring device according to an embodiment of the present invention, and FIG. 2 is a drawing for explaining a measuring principle of a measuring apparatus of FIG. 1.

A measuring apparatus 100, referring to FIG. 1 and FIG. 2, is a measuring apparatus for measuring characteristics such as a density of micro-fluid or particles floating therein and includes a micro-tube 110, an actuator 120 and a tuning fork 130.

The micro-tube 110, as shown in FIG. 1, contains micro-fluid or the like to be measured, and is vibrated by the actuator 120. In particular, the micro-tube 110 may be formed by a plastic working in which a glass capillary tube is melted by a laser heating and is then pulled, i.e., a laser pulling forming process. Accordingly, compared to a conventional MEMS process, the manufacturing process is simple and thus the manufacturing cost can be reduced and the yielding rate can be increased. Further, by the laser pulling forming process, the diameter and the length of the micro-tube 110 vary depending on pulling amount, so the micro-tube 110 having various conditions can be provided.

Moreover, the micro-tube 110 can be made as a resonator having various resonant frequencies by applying a tension or regulating a resonant length. In detail, the resonant frequency can be tuned by applying a longitudinal tension to the micro-tube 110, or by regulating a length I between a first node A which the actuator 120 contacts and a second node B which an end of a cantilever 131 of the tuning fork 130 contacts.

The actuator 120, as shown in FIG. 1, is an element for vibrating the micro-tube 110. For example, the actuator 120 may be a piezo-actuator which contacts the surface of the micro-tube 110 (referring to the point A) and applies pressure in a specific direction.

The tuning fork 130 converts the vibration of the micro-tube 110 into an electrical signal. For example, the tuning fork 130 may be formed such that an end of the cantilever 131 contacts the surface of the micro-tube 110 (referring to the point B) and may be a quartz tuning fork which is made of quartz to have a piezoelectric effect. The quartz tuning fork 130, as shown in FIG. 2, receives Fy component among the reactive forces generated by a longitudinal axis extension Ft (Fx, Fy) which is applied to the micro-tube 110 by the piezo-actuator 120 and converts the same into an electrical signal.

Characteristics such as a density or particles of the micro-fluid can be measured by a real time resonant frequency change measurement via a frequency sweep method or a feedback control using the converted electrical signal. Accordingly, the measuring apparatus 100 according to an embodiment of the present invention may be used as an apparatus for measuring a density of micro-fluid, an apparatus for analyzing micro particles in the micro-fluid or an electrophoresis equipment in the micro-fluid.

In this regard, the electrical signal may be transmitted to the outside via a voltage-current converter (not shown).

The measuring apparatus 100 according to an embodiment of the present invention, as shown in FIG. 1 and FIG. 2, may further include a first injection capillary tube 141, a second injection capillary tube 142 and a fixing portion 150. The first and the second injection capillary tubes 141 and 142 respectively communicate with both ends of the micro-tube 110 and inject micro-fluid or the like which will be measured, and the fixing portions 150 fix the first and the second injection capillary tubes 141 and 142 to an outer fixing member. Accordingly, the micro-fluid or the like is injected into the micro-tube 110 via the first and the second injection capillary tubes 141 and 142 and at the same time both ends of the micro-tube 110 can be fixed by the first and the second injection capillary tubes 141 and 142 and the fixing portions 150.

Furthermore, the micro-tube 110 and the first and the second injection capillary tubes 141 and 142 may be integrally formed. In this case, the micro-tube 110 may be an elongated portion in case that the micro-tube 110 is formed by melting a glass capillary tube by a laser heating and then pulling the same to be elongated, and the first and the second injection capillary tubes 141 and 142 may be both end portions of the glass capillary tube which are not elongated by being pulled.

Also, the non-elongated end portions of the first and the second injection capillary tubes 141 and 142 can be easily connected to fluid connectors (not shown) of external fluid equipments so as to be supplied with micro-fluid which will be measured.

As such, the measuring apparatus 100 according to an embodiment of the present invention has the following effects.

According to an embodiment of the present invention, the conventional optical measurement device can be replaced with the tuning fork 130, so the volume can be reduced compared to that of the optical measuring device, and thus it can be easily implanted to other measuring system and can be easily packed in vacuum.

Also, according to an embodiment of the present invention, since the micro-tube is made by a plastic working in which the glass capillary tube is melted by laser hearing and then is pulled, the manufacturing process is simple compared to the MEMS process of the conventional art so that the manufacturing cost can be reduced ant the yielding rate can be enhanced.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A measuring apparatus for measuring micro-fluid or floating particles therein comprising:
   a micro-tube containing the micro-fluid;
   an actuator vibrating the micro-tube; and
   a tuning fork converting vibration of the micro-tube into an electrical signal.

2. The measuring apparatus of claim 1, wherein the micro-tube is formed by a plastic working in which a glass capillary tube is melted by a laser heating and is then pulled.

3. The measuring apparatus of claim 1, further comprising:
   a first injection capillary tube and a second injection capillary tube respectively communicating with both ends of the micro-tube so as to inject the micro-fluid into the micro-tube; and
   fixing portions fixing the first and the second injection capillary tubes.

4. The measuring apparatus of claim 3, wherein the actuator is a piezo-injector which contacts a surface of the micro-tube and applies pressure in a specific direction.

5. The measuring apparatus of claim 4, wherein the tuning fork is a quartz tuning fork which contacts a surface of the micro-tube and is made of quartz to have a piezoelectric effect.

6. The measuring apparatus of claim 5, wherein the quartz tuning fork receives Fy component among reactive forces generated by a longitudinal axis extension Ft (Fx, Fy) which is applied to the micro-tube by the piezo-actuator and converts the same into an electrical signal.

7. The measuring apparatus of claim 3, wherein the micro-tube and the first and the second injection capillary tube are integrally formed.

8. The measuring apparatus of claim 7, wherein the micro-tube is an elongated portion in case that the micro-tube is formed by melting a glass capillary tube by a laser heating and then pulling the same to be elongated, and the first and the second injection capillary tubes are both end portions of the glass micro-tube which are not elongated by being pulled.

* * * * *